(12) United States Patent
Kurose et al.

(10) Patent No.: US 9,057,103 B2
(45) Date of Patent: Jun. 16, 2015

(54) METHOD FOR DETECTING MUTATIONS AT IL28B AND ITPA

(75) Inventors: Kaoru Kurose, Kyoto (JP); Toshiya Hosomi, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 0 days.

(21) Appl. No.: 13/617,591

(22) Filed: Sep. 14, 2012

(65) Prior Publication Data

US 2013/0309663 A1 Nov. 21, 2013

Related U.S. Application Data

(60) Provisional application No. 61/537,851, filed on Sep. 22, 2011.

(30) Foreign Application Priority Data

Sep. 15, 2011 (JP) .................................. 2011-202261

(51) Int. Cl.
*C12Q 1/68* (2006.01)
*C07H 21/02* (2006.01)
*C07H 21/04* (2006.01)

(52) U.S. Cl.
CPC ........ *C12Q 1/6881* (2013.01); *C12Q 2600/156* (2013.01); *C12Q 1/6876* (2013.01); *C12Q 2563/107* (2013.01); *C12Q 1/6883* (2013.01); *C12Q 2600/106* (2013.01)

(58) Field of Classification Search
None
See application file for complete search history.

(56) References Cited

U.S. PATENT DOCUMENTS

| | | | |
|---|---|---|---|
| 6,582,908 B2 * | 6/2003 | Fodor et al. ........................ | 506/9 |
| 2002/0106653 A1 | 8/2002 | Kurane et al. | |
| 2003/0022177 A1 * | 1/2003 | Wittwer et al. ................... | 435/6 |
| 2009/0176231 A1 | 7/2009 | Hirai et al. | |
| 2011/0165124 A1 * | 7/2011 | Bochud et al. ............... | 424/85.7 |

FOREIGN PATENT DOCUMENTS

| | | |
|---|---|---|
| CN | 101548022 A | 9/2009 |
| EP | 2055774 A1 | 5/2009 |
| JP | 2002-119291 A | 4/2002 |
| WO | 02/14555 A2 | 2/2002 |
| WO | 2010/144946 A1 | 12/2010 |

OTHER PUBLICATIONS

Partial Search Report issued in related European Patent Application No. 12184426.0 dated Nov. 7, 2012.
Melis et al., "Simultaneous Genotyping of rs12979860 and rs8099917 Variants Near the IL28B Locus Associated with HCV Clearance and Treatment Response," The Journal of Molecular Diagnostics, 13: 446-451 (2011).
Lin et al., "IL28B SNP rs12979860 Is a Critical Predictor for On-Treatment and Sustained Virologic Response in Patients with Hepatitis C Virus Genotype-1 Infection," PLoS One, 6: e18322 (2011).
Ito et al., "The rs8099917 Polymorphism, When Determined by a Suitable Genotyping Method, Is a Better Predictor for Response to Pegylated Alpha Interferon/Ribavirin Therapy in Japanese Pateints than Other Single Nucleotide Polymorphisms Associated with Interleukin-28B," Journal of Clinical Microbiology, 49: 1853-1860 (2011).
Tani et al., "Quantification of Genetically Modified Soybean by Quenching Probe Polymerase Chain Reaction," Journal of Agricultural and Food Chemistry, 53: 2535-2540 (2005).
Tanaka et al "Genome-wide association of IL28B with response to pegylated interferon-alpha and ribavirin therapy for chronic hepatitis C," Nature Genetics, 41: 1105-1109 (2009).
Aparicio et al., "IL28B SNP rs8099917 Is Strongly Associated with Pegylated Interferon-alpha and Ribavirin Therapy Treatment Failure in HCV/HIV-1 Coinfected Patients," PLoS One, 5: e13771 (2010).
Sakamoto et al., "ITPA gene variant protects against anemia induced by pegylated interferon-alpha and ribavirin therapy for Japanese patients with chronic hepatitis c," Hepatology Research, 40: 1063-1071 (2010).
Ochi et al., "ITPA Polymorphism Affects Ribavirin-Induced Anemia and Outcomes of Therapy-A Genome-Wide Study of Japanese HCV Virus Patients," Gastroenterology, 139: 1190-1197 (2010).
Suzuki et al., "Influence of ITPA Polymorphisms on Decreases of Hemoglobin During Treatment with Pegylated Interferon, Ribavirin, and Telaprevir," Hepatology, 53: 415-421 (2011).
Office Action issued in corresponding Chinese Patent Application No. 201210353290.9 dated Feb. 2, 2015.

* cited by examiner

*Primary Examiner* — Carla Myers
(74) *Attorney, Agent, or Firm* — Morgan, Lewis & Bockius LLP

(57) ABSTRACT

The disclosure relates to probes for detecting a polymorphism in the IL28B gene and in the ITPA gene, and methods of use thereof.

10 Claims, 4 Drawing Sheets

(A)

(B)

SEQUENCE LISTING

<160> NUMBER OF SEQ ID NOS: 19

<210> SEQ ID NO 1
<211> LENGTH: 601
<212> TYPE: DNA
<213> ORGANISM: Homo sapiens

<400> SEQUENCE: 1

```
tgaaaaatac acaaaaacat aaagaaaaa aaacatcacc tataacttca ccatcctcct      60
ctcatccctc atcccacttc tggaacaaat cgtcccaata cataggaatt ttccatgtgt     120
ttatttgtgc atatgttttc tgactaccaa agtaacactt gttccttgta aaagattcca    180
```

```
tccatacaaa aacatacaac atggagagtt aaagtaagtc ttgtatttca cctcctggag    240
gtaaatattt tttaacaatt tgtcactgtt cctccttttg ttttcctttc tgtgagcaat    300
ktcacccaaa ttgaaccat gctgtataca gtttggtagc tggcttttta tgtcttacca    360
```
(Note: corrected per image)
```
ktcacccaaa ttgaaccat gctgtataca gtttggtagc tggcttttta tgtcttacca    360
ttatctctca tttgcattct cccacatctt taattatagc gtatcagtta gggcccagca    420
ggaaacagat ggcccgtcaa tttaggataa tttgaggtgg ggttgatacc agaagccttt    480
ataaagcgat tggatagtaa aggcaaatga caagagctag tgcaagctcc tggggccagc    540
atgggtgagg ggcctcatcc acaggcctaa aggaagggga gagggttgag ggtgtgcatg    600
t                                                                   601
```

<210> SEQ ID NO 2
<211> LENGTH: 501
<212> TYPE: DNA
<213> ORGANISM: Homo sapiens

<400> SEQUENCE: 2

```
acaagcagag acctgacgta aagagatag agaagcaagg agatggaagg ggctggcttg     60
ctggggtggg accctgaaag ccggggtgag gcccacaggc ctgagttggt aagctttagg    120
agatgggcag cagagttatc gatgagaaag gcggatgaca gctcacgtgc tcacatggag    180
aatcactaga tggtgataag tgttctcttt tctcttggaa caggtcgttc agattctagg    240
agataagttt vcatgcactt tggtggcaca gaaaattgac cgtatgtctc tgttttgttt    300
tattttaaaa agatggttgg atttctctgt cttcctgtga cctgactttc tgtgtgtctg    360
tttccctgat aagtgccgga gtaccagggg gagccggatg agatttccat acagaaatgt    420
caggaggcag ttcgccaggt gcttgccctg cccttgtccc acacttgctc ttcttgtcca    480
ggtagcttcc agggcctgcg c                                             501
```

<210> SEQ ID NO 3
<211> LENGTH: 18
<212> TYPE: DNA
<213> ORGANISM: Artificial Sequence
<220> FEATURE:
<223> OTHER INFORMATION: probe

<400> SEQUENCE: 3
ctgtgagcaa tgtcaccc                                                  18

<210> SEQ ID NO 4
<211> LENGTH: 18
<212> TYPE: DNA
<213> ORGANISM: Artificial Sequence
<220> FEATURE:
<223> OTHER INFORMATION: probe

<400> SEQUENCE: 4
gcatgtaaac ttatctcc                                                  18

<210> SEQ ID NO 5
<211> LENGTH: 22
<212> TYPE: DNA
<213> ORGANISM: Artificial Sequence
<220> FEATURE:
<223> OTHER INFORMATION: probe

<400> SEQUENCE: 5
tctaggagat aagtttccat gc                                             22

<210> SEQ ID NO 6
<211> LENGTH: 36
<212> TYPE: DNA
<213> ORGANISM: Artificial Sequence
<220> FEATURE:
<223> OTHER INFORMATION: primer

<400> SEQUENCE: 6
caacatggag agttaaagta agtcttgtat ttcacc            36

<210> SEQ ID NO 7
<211> LENGTH: 29
<212> TYPE: DNA
<213> ORGANISM: Artificial Sequence
<220> FEATURE:
<223> OTHER INFORMATION: primer

<400> SEQUENCE: 7
cagctaccaa actgtataca gcatggttc                    29

<210> SEQ ID NO 8
<211> LENGTH: 26
<212> TYPE: DNA
<213> ORGANISM: Artificial Sequence
<220> FEATURE:
<223> OTHER INFORMATION: primer

<400> SEQUENCE: 8
aagtgttctc ttttctcttg gaacag                       26

<210> SEQ ID NO 9
<211> LENGTH: 25
<212> TYPE: DNA
<213> ORGANISM: Artificial Sequence
<220> FEATURE:
<223> OTHER INFORMATION: primer

<400> SEQUENCE: 9
agagacatac ggtcaattttt ctgtg                       25

<210> SEQ ID NO 10
<211> LENGTH: 37
<212> TYPE: DNA
<213> ORGANISM: Artificial Sequence
<220> FEATURE:
<223> OTHER INFORMATION: oligonucleotide

<400> SEQUENCE: 10
tggttccaat ttgggtgaca ttgctcacag aaaggaa           37

<210> SEQ ID NO 11
<211> LENGTH: 37
<212> TYPE: DNA
<213> ORGANISM: Artificial Sequence
<220> FEATURE:
<223> OTHER INFORMATION: oligonucleotide

<400> SEQUENCE: 11
tggttccaat ttgggtgaaa ttgctcacag aaaggaa           37

<210> SEQ ID NO 12
<211> LENGTH: 20
<212> TYPE: DNA
<213> ORGANISM: Artificial Sequence
<220> FEATURE:
<223> OTHER INFORMATION: probe

```
<400> SEQUENCE: 12
caatttgggt gacattgctc                                                   20

<210> SEQ ID NO 13
<211> LENGTH: 37
<212> TYPE: DNA
<213> ORGANISM: Artificial Sequence
<220> FEATURE:
<223> OTHER INFORMATION: oligonucleotide

<400> SEQUENCE: 13
ttcctttctg tgagcaatgt cacccaaatt ggaacca                                 37

<210> SEQ ID NO 14
<211> LENGTH: 37
<212> TYPE: DNA
<213> ORGANISM: Artificial Sequence
<220> FEATURE:
<223> OTHER INFORMATION: oligonucleotide

<400> SEQUENCE: 14
ttcctttctg tgagcaattt cacccaaatt ggaacca                                 37

<210> SEQ ID NO 15
<211> LENGTH: 60
<212> TYPE: DNA
<213> ORGANISM: Artificial Sequence
<220> FEATURE:
<223> OTHER INFORMATION: oligonucleotide

<400> SEQUENCE: 15
ggtcaatttt ctgtgccacc aaagtgcatg taaacttatc tcctagaatc tgaacgacct       60

<210> SEQ ID NO 16
<211> LENGTH: 60
<212> TYPE: DNA
<213> ORGANISM: Artificial Sequence
<220> FEATURE:
<223> OTHER INFORMATION: oligonucleotide

<400> SEQUENCE: 16
ggtcaatttt ctgtgccacc aaagtgcatg gaaacttatc tcctagaatc tgaacgacct       60

<210> SEQ ID NO 17
<211> LENGTH: 23
<212> TYPE: DNA
<213> ORGANISM: Artificial Sequence
<220> FEATURE:
<223> OTHER INFORMATION: probe

<400> SEQUENCE: 17
cagattctag gagataagtt tcc                                               23

<210> SEQ ID NO 18
<211> LENGTH: 25
<212> TYPE: DNA
<213> ORGANISM: Artificial Sequence
<220> FEATURE:
<223> OTHER INFORMATION: oligonucleotide

<400> SEQUENCE: 18
tggaaactta tctcctagaa tctga                                             25

<210> SEQ ID NO 19
<211> LENGTH: 25
```

```
<212> TYPE: DNA
<213> ORGANISM: Artificial Sequence
<220> FEATURE:
<223> OTHER INFORMATION: oligonucleotide

<400> SEQUENCE: 19
tgtaaactta tctcctagaa tctga                                    25
```

METHOD FOR DETECTING MUTATIONS AT IL28B AND ITPA

CROSS-REFERENCE TO RELATED APPLICATION

This application claims priorities from Japanese Patent Application No. 2011-202261 filed on Sep. 15, 2011 and U.S. Provisional Application No. 61/537,851 filed on Sep. 22, 2011, the entire subject matter of which is incorporated herein by reference in its entirety.

SEQUENCE LISTING SUBMISSION VIA EFS-WEB

A computer readable text file, entitled "SequenceListing.txt," created on or about Sep. 15, 2012 with a file size of about 2 kb contains the sequence listing for this application and is hereby incorporated by reference in its entirety.

TECHNICAL FIELD

The present invention relates to a method for detecting mutations at IL28B (rs8099917) and ITPA (rs1127354), nucleic acid probes and a kit therefor.

BACKGROUND ART

Hepatitis C is a viral hepatitis caused by infection with hepatitis C virus (HCV). In Japan, the number of patients suffering from HCV infection is about 2,000,000, and progression to chronic hepatitis occurs in 60 to 80% of HCV patients. In cases where treatment is not carried out and chronic hepatitis is maintained for 10 to 30 years, progression to liver cirrhosis/liver cancer occurs in 30 to 40% of patients. Examples of antiviral therapies for removal of HCV include interferon therapy, whose treatment results have been improved by the combined use of ribavirin and the pegylation of interferon.

As a result of analysis of about 900,000 sites in human genes, which are said to be different among individuals, in 314 Japanese patients for whom the pegylated interferon+ribavirin combination therapy is effective or ineffective, it has been reported that SNPs existing in the gene for IL28B, which is an interferon (IFN), and in the vicinity of the gene are involved in the therapeutic effect (Nature Genetics 41, 1105-1109 (2009)). Further, it has been reported that out of the 6 SNPs that were predicted to be involved in the effect of the pegylated interferon+ribavirin combination therapy, the SNP identified as rs8099917 has the largest influence on the therapeutic effect (PLoS One. 2010 Oct. 29; 5(10):e13771).

Ribavirin-induced anemia is a major factor that forces anti-hepatitis C virus (HCV) therapy to be terminated or reduced (Hepatol Res. 2010 November; 40(11):1063-1071). As a result of the evaluation of the clinical significance of ITPA gene variations in Japanese hepatitis C patients treated with the pegylated interferon (PEG-IFN)/ribavirin combination therapy, it has been reported that rs1127354, which is a functional SNP in an ITPA exon, is a useful predictive factor for ribavirin-induced anemia (Gastroenterology. 2010 October; 139(4):1190-7. Epub 2010 Jul. 14).

PLoS One. 2010 Oct. 29; 5(10): e13771 reports that mutation at IL28B (rs8099917) is strongly involved in the effect of the pegylated interferon/ribavirin combination therapy in hepatitis C patients, and detection of the presence/absence of a mutation at IL28B (rs8099917) was carried out by sequence analysis. HePATOLOGY, Vol. 53, Issue 2, pages 415-421, 2011 reports that mutation at ITPA (rs1127354) is strongly involved in anemia during treatment with the pegylated interferon/ribavirin combination therapy, and detection of the presence/absence of a mutation at ITPA (rs1127354) was carried out by sequence analysis.

However, it is very laborious and costly to carry out genomic DNA extraction from whole blood at actual clinical sites for investigating SNP variation in hepatitis C patients as described in PLoS One. 2010 Oct. 29; 5(10): e13771 and HePATOLOGY, Vol. 000, No. 000, 2011. Therefore, it is assumed that the demand for a technology with which the presence/absence of mutations can be automatically and directly assayed using whole blood will increase. Further, because of the involvement of IL28B (rs8099917) and ITPA (rs1127354) in the effect of the pegylated interferon/ribavirin combination therapy, it is highly likely that a technology that allows the simultaneous assay of the presence/absence of mutations in IL28B (rs8099917) and ITPA (rs1127354) will be required in the future in the clinical field, but such simultaneous detection cannot be done by either PLoS One. 2010 Oct. 29; 5(10): e13771 or HePATOLOGY, Vol. 000, No. 000, 2011, since detection of the presence/absence of mutations in IL28B (rs8099917) and ITPA (rs1127354) was carried out by sequence analysis.

JP 2002-119291 A describes a method wherein a nucleic acid probe labeled with a fluorescent dye is hybridized with a target nucleic acid and the amount of decrease in the luminescence from the fluorescent dye is measured. However, in cases where a nucleic acid probe labeled with a fluorescent dye is hybridized with a target nucleic acid and the amount of decrease in the luminescence from the fluorescent dye is measured, the sequence of the nucleic acid probe cannot be arbitrary and an appropriate sequence must be found for each mutation.

SUMMARY

The present disclosure relates to probes effective for detecting a polymorphism rs8099917 in the IL28B gene and a polymorphism rs1127354 in the ITPA gene. The disclosure also relates to a method for detecting the polymorphism rs8099917 in the IL28B gene and the polymorphism rs1127354 in the ITPA gene, and a kit therefor.

As described herein, by designing probes based on a specific region comprising the polymorphism rs8099917 in the IL28B gene and a specific region comprising the polymorphism rs1127354 in the ITPA gene, and detecting changes in a signal due to formation of a hybrid of the probes with target nucleic acids or due to dissociation of the probes from target nucleic acids, mutations at these sites may be detected, thereby completing the present invention.

That is, some embodiments of the present disclosure are as follows.

(1) A probe for detecting a polymorphism in the IL28B gene, comprising the fluorescently labeled oligonucleotide P1 or P1' below:

(P1) an oligonucleotide comprising a nucleotide sequence of 7 to 28 consecutive nucleotides containing nucleotides 301 to 307 in SEQ ID NO:1 or a homologous sequence thereof, wherein the nucleotide corresponding to the nucleotide at position 307 is a cytosine and is labeled with a fluorescent dye;

(P1') an oligonucleotide comprising a nucleotide sequence of 7 to 28 consecutive nucleotides containing nucleotides 301 to 307 in SEQ ID NO:1 or a nucleotide sequence which hybridizes with the complementary strand of SEQ ID NO: 1 under stringent conditions, wherein the nucleotide corresponding to the nucleotide at position 307 is a cytosine and is labeled with a fluorescent dye.

(2) A probe for detecting a polymorphism in the ITPA gene, comprising at least one fluorescently labeled oligonucleotide selected from P2 to P3' below:

(P2) an oligonucleotide comprising a complement of a nucleotide sequence of 13 to 28 consecutive nucleotides containing nucleotides 239 to 251 in SEQ ID NO:2 or a homologous sequence thereof, wherein the nucleotide corresponding (i.e. complementary) to the nucleotide at position 239 is a cytosine and is labeled with a fluorescent dye;

(P2') an oligonucleotide comprising a nucleotide sequence which hybridizes with a nucleotide sequence of 13 to 28 consecutive nucleotides containing nucleotides 239 to 251 in SEQ ID NO:2 under stringent conditions, wherein the nucleotide corresponding (i.e. complementary) to the nucleotide at position 239 is a cytosine and is labeled with a fluorescent dye;

(P3) an oligonucleotide comprising a nucleotide sequence of 6 to 42 consecutive nucleotides containing nucleotides 251 to 256 in SEQ ID NO:2 or a homologous sequence thereof, wherein the nucleotide corresponding to the nucleotide at position 256 is a cytosine and is labeled with a fluorescent dye;

(P3') an oligonucleotide comprising a nucleotide sequence of 6 to 42 consecutive nucleotides containing nucleotides 251 to 256 in SEQ ID NO:2 or a nucleotide sequence which hybridizes with the complementary strand of SEQ ID NO: 2 under stringent conditions, wherein the nucleotide corresponding to the nucleotide at position 256 is a cytosine and is labeled with a fluorescent dye.

(3) The probe according to (1), wherein
said oligonucleotides P1 and P1' have the nucleotide corresponding to the nucleotide at position 307 labeled with a fluorescent dye at the first, second or third position counted from the 3'-end;
said oligonucleotides P2 and P2' have the nucleotide corresponding (i.e. complementary) to the nucleotide at position 239 labeled with a fluorescent dye at the first, second or third position counted from the 3'-end; and
said oligonucleotides P3 and P3' have the nucleotide corresponding to the nucleotide at position 256 labeled with a fluorescent dye at the first, second or third position counted from the 3'-end.

(4) The probe according to (1), wherein
said oligonucleotides P1 and P1' have the nucleotide corresponding to the nucleotide at position 307 labeled with a fluorescent dye at the 3'-end;
said oligonucleotides P2 and P2' have the nucleotide corresponding (i.e. complementary) to the nucleotide at position 239 labeled with a fluorescent dye at the 3'-end; and
said oligonucleotides P3 and P3' have the nucleotide corresponding to the nucleotide at position 256 labeled with a fluorescent dye at the 3'-end.

(5) The probe according to (1), wherein said fluorescently labeled oligonucleotide emits fluorescence when said oligonucleotide is not hybridized with a target sequence, and the fluorescence intensity decreases or increases when said oligonucleotide is hybridized with said target sequence.

(6) The probe according to (5), wherein said fluorescently labeled oligonucleotide emits fluorescence when said oligonucleotide is not hybridized with a target sequence, and the fluorescence intensity decreases when said oligonucleotide is hybridized with said target sequence.

(7) The probe according to (1), wherein
said oligonucleotides P1 and P1' have 7 to 23 consecutive nucleotides;
said oligonucleotides P2 and P2' have 13 to 23 consecutive nucleotides; and
said oligonucleotides P3 and P3' have 6 to 27 consecutive nucleotides.

(8) The probe according to (1), wherein
said oligonucleotides P1 and P1' have 7 to 18 consecutive nucleotides;
said oligonucleotides P2 and P2' have 13 to 18 consecutive nucleotides; and
said oligonucleotides P3 and P3' have 6 to 22 consecutive nucleotides.

(9) The probe according to (1), wherein said probe is a probe for melting curve analysis.

(10) A method for detecting a polymorphism in the IL28B gene using the probe for the IL28B gene according to (1). The method may be conducted on a sample comprising nucleic acid which may contain said polymorphism and comprises contacting the probe with said sample and detecting the presence or absence of the polymorphism. The invention also extends to use of said probe for detecting said polymorphism.

(11) The method according to (10) for detecting polymorphisms in the IL28B gene and the ITPA gene by using the probe for the IL28B gene according to of (1) and the probe for the ITPA gene according to (2). The invention also extends to use of said probes for detecting said polymorphisms.

(12) A method for detecting polymorphisms in the IL28B gene and the ITPA gene separately or in a single reaction system, comprising the Steps (I) to (IV) below:

(I) adding the probe for the IL28B gene according to (1) and the probe for the ITPA gene according to (2) to a sample containing DNA and allowing hybridization of said probe with said DNA;

(II) changing the temperature to dissociate the hybridization complex between said DNA and said probe, and measuring the fluctuation of the signal due to said dissociation of said hybridization complex;

(III) analyzing said fluctuation of the signal to determine the Tm value; and (IV) determining based on said Tm value the presence/absence of said polymorphisms of interest or the abundance ratios of the nucleotide sequences having said polymorphisms.

(13) The method according to (12), further comprising amplifying DNA before Step (I) or at the same time as Step (I).

(14) A method for judging (or predicting) a pharmacological effect of a therapeutic agent against hepatitis C virus, comprising detecting polymorphisms in the IL28B gene and the ITPA gene separately or in a single reaction system by the method according to (11) and judging (or predicting) the resistance to said agent or judging (or predicting) a pharmacological effect of said agent based on the presence/absence of said polymorphisms of interest. Said method may be performed in a sample from a subject (e.g. a human) in relation to whom the judgement/prediction is to be made. A sample (as used herein) comprises nucleic acid (e.g. DNA) which may contain said polymorphism.

(15) A reagent kit for detecting polymorphisms in the IL28B gene and the ITPA gene separately or in a single reaction system, comprising the probe for the IL28B gene according to (1) and the probe for the ITPA gene according to (2).

(16) The reagent kit according to (15), further comprising:
a primer for amplifying a region comprising a sequence, in the nucleotide sequence shown in SEQ ID NO:1 in the IL28B gene, with which said oligonucleotide P1 or P1'*hybridizes*; *and/or*
a primer for amplifying a region comprising a sequence, in the nucleotide sequence shown in SEQ ID NO:2 in the ITPA gene, with which said oligonucleotide P2, P2', P3, or P3' hybridizes. The invention also extends to the use of said kit for detecting said polymorphism(s).

By including the probe of the present disclosure in a gene amplification system such as PCR and only carrying out Tm analysis after the gene amplification reaction, typing of the polymorphism rs8099917 in the IL28B gene and the polymorphism rs1127354 in the ITPA gene may be carried out. Further, since whole blood, an oral mucosa suspension and the like may be directly tested, the labour and the costs may be reduced.

The probe of the present disclosure has high specificity.

By using the method of the present disclosure, even in cases where PCR is carried out, the amplification product does not need to be extracted, so that there is hardly any risk of contamination. Further, since the method of the present disclosure may be carried out by a simple procedure, it may be easily automated.

By using the method of the present disclosure, the polymorphism rs8099917 in the IL28B gene and the polymorphism rs1127354 in the ITPA gene may be simultaneously detected.

MODE FOR CARRYING OUT THE INVENTION

<1> Probes and Detection Method

Figure 1:
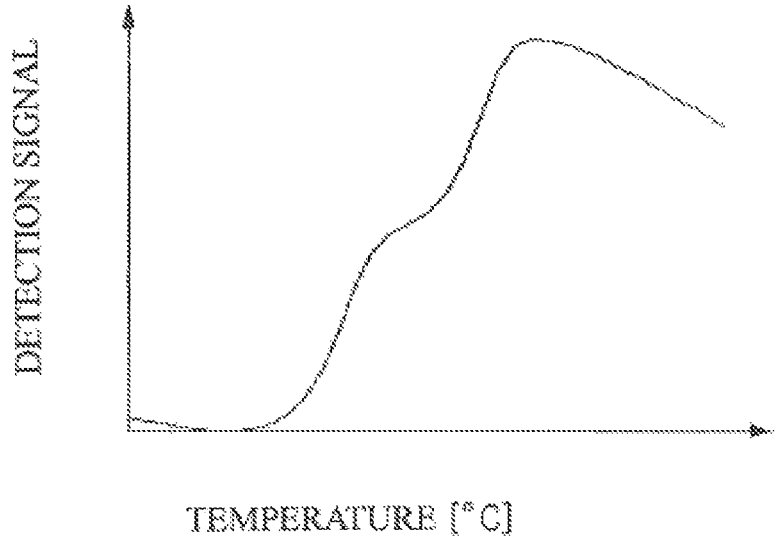
FIG. 1 is a diagram showing examples of (A) a melting curve of a nucleic acid mixture and (B) a differential melting curve.
Figure 1:
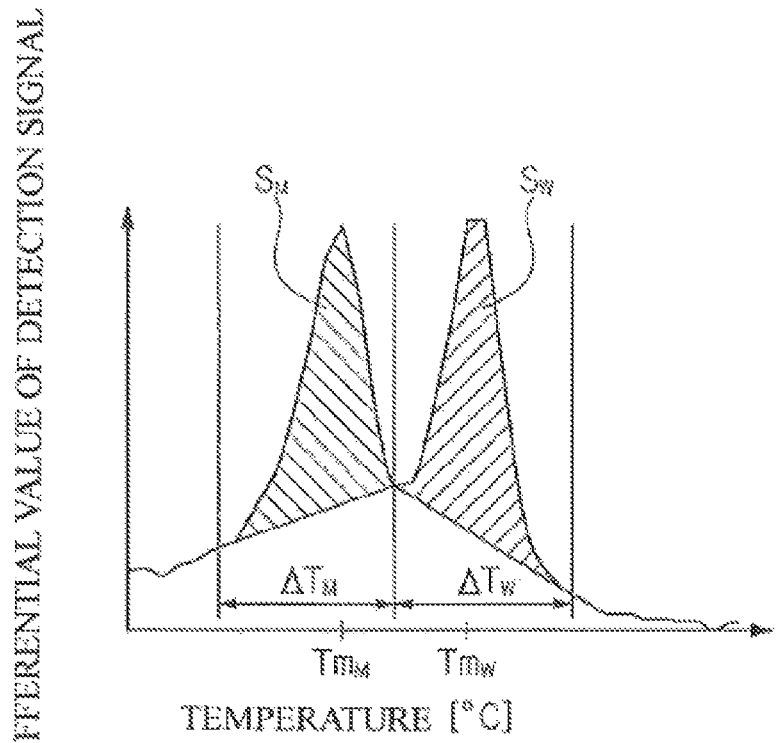

The (P1) probe of the present disclosure is a probe for detecting the polymorphism rs8099917 in the IL28B gene, and is composed of an oligonucleotide comprising a nucleotide sequence of 7 to 28 consecutive nucleotides containing nucleotides 301 to 307 in SEQ ID NO:1 or a homologous sequence thereof. In some embodiments, the nucleotide corresponding to the nucleotide at position 307 is a cytosine and is labeled with a fluorescent dye. As referred to in this context, the homologous sequence is homologous to SEQ ID NO:1 or the recited portion of SEQ ID NO:1. The 7 to 28 nucleotides are all contained, consecutively in SEQ ID NO:1 or its homologous sequence.

The (P1') probe of the present disclosure is a probe for detecting the polymorphism rs8099917 in the IL28B gene, and is composed of an oligonucleotide comprising a nucleotide sequence of 7 to 28 consecutive nucleotides containing nucleotides 301 to 307 in SEQ ID NO:1 or a nucleotide sequence which hybridizes with the complementary strand of SEQ ID NO: 1 under stringent conditions, wherein the nucleotide corresponding to the nucleotide at position 307 is a cytosine and is labeled. In some embodiments, the nucleotide corresponding to the nucleotide at position 307 is labeled with a fluorescent dye. As referred to in this context, the hybridizing sequence hybridizes with the complementary strand of SEQ ID NO:1 or the recited portion of SEQ ID NO:1. The 7 to 28 nucleotides are all contained, consecutively in SEQ ID NO:1 or the hybridizing sequence.

The polymorphism rs8099917 in the IL28B gene described herein is located at nucleotide position 301 in SEQ ID NO:1. The rs number represents a registration number for the dbSNP database curated by the National Center for Biotechnology Information (//www.ncbi.nlm.nih.gov/projects/SNP/). The nucleotide at position 301 in SEQ ID NO:1 is represented as k, which represents T in the wild-type and G in the mutant type. For example, in the probes (P1) and (P1') of the present disclosure, the nucleotide at position 301 in SEQ ID NO:1 is G, which is the mutant type.

In additional embodiments, the probe for detecting a polymorphism in the IL28B gene as described herein comprises a labeled oligonucleotide P1 or P1' below:

(P1) an oligonucleotide of 7 to 28 nucleotides comprising a sequence at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% identical to nucleotides 301 to 307 in SEQ ID NO:1, wherein the nucleotide corresponding to the nucleotide at position 307 in SEQ ID NO:1 is a cytosine;

(P1') an oligonucleotide of 7 to 28 nucleotides which hybridizes with the complementary nucleotide sequence to the nucleotides 301 to 307 in SEQ ID NO: 1 under stringent conditions, wherein the nucleotide complementary to the nucleotide at position 307 in SEQ ID NO:1 is a cytosine.

The (P1) and (P1') probes of the present disclosure may be prepared in the same manner as the probe described in JP 2002-119291 A except that the probes of the present disclosure have the above-described specific sequence in the nucleotide sequence shown in SEQ ID NO:1. Examples of the length of the probes (P1) and (P1') include 7 to 48 consecutive nucleotides, 7 to 28 consecutive nucleotides, 7 to 23 consecutive nucleotides and 7 to 18 consecutive nucleotides.

Examples of the nucleotide sequences of the (P1) and (P1') probes used in the present disclosure include 5'-ctgtgagcaat-Gtcaccc-3' (SEQ ID NO:3), and the nucleotide denoted by the upper case letter G corresponds to the nucleotide at position 301.

The (P2) probe of the present disclosure is a probe for detecting the polymorphism rs1127354 in the ITPA gene, and is composed of an oligonucleotide comprising a complement of a nucleotide sequence of 13 to 28 consecutive nucleotides containing nucleotides 239 to 251 in SEQ ID NO:2 or a homologous sequence thereof, wherein the nucleotide corresponding or complementary to the nucleotide at position 239 is a cytosine. In some embodiments, the nucleotide corresponding or complementary to the nucleotide at position 239 is labeled with a fluorescent dye. As referred to in this context, the homologous sequence is homologous to SEQ ID NO:2 or the recited portion of SEQ ID NO:2 (i.e. the oligonucleotide comprises a complement of said homologous sequence). The 13 to 28 nucleotides are all contained, consecutively in SEQ ID NO:2 or its homologous sequence.

The (P2') probe of the present disclosure is a probe for detecting the polymorphism rs1127354 in the ITPA gene, and is composed of an oligonucleotide comprising a nucleotide sequence which hybridizes with a nucleotide sequence of 13 to 28 consecutive nucleotides containing nucleotides 239 to 251 in SEQ ID NO:2 under stringent conditions, wherein the nucleotide corresponding or complementary to the nucleotide at position 239 is a cytosine. In some embodiments, the nucleotide corresponding or complementary to the nucleotide at position 239 is labeled with a fluorescent dye. The 13 to 28 nucleotides are all contained, consecutively in SEQ ID NO:2.

The polymorphism rs1127354 in the ITPA gene described herein is located at nucleotide position 251 in SEQ ID NO:2. The nucleotide at position 251 in SEQ ID NO:2 is represented as v, which represents C in the wild-type and A in the mutant type. Three types of nucleotides, C/A/G, are registered in the SNP site of NCBI for the polymorphism rs1127354 in the ITPA gene, and it is described that the allele frequency of C is 87.5% and the allele frequency of A is 12.5% in the Japanese population (no Japanese person has the G-type allele). Further, only one person (tissue) who reported the existence of G carried out the assay (this also applies to the case of the P3 probe). For example, the (P2) or (P2') probe of the present disclosure is complementary to the nucleotide sequence shown in SEQ ID NO:2 wherein the nucleotide at position 251 is A, which corresponds to the mutant type.

In additional embodiments, the probe for detecting a polymorphism in the ITPA gene as described herein comprises at least one labeled oligonucleotide selected from P2 to P3' below:

(P2) an oligonucleotide of 13 to 28 nucleotides comprising a sequence at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% identical to a complementary nucleotide sequence to nucleotides 239 to 251 in SEQ ID NO:2, wherein the nucleotide complementary to the nucleotide at position 239 in SEQ ID NO:2 is a cytosine and is labeled;

(P2') an oligonucleotide of 13 to 28 nucleotides which hybridizes with the nucleotides 239 to 251 in SEQ ID NO:2 under stringent conditions, wherein the nucleotide complementary to the nucleotide at position 239 in SEQ ID NO:2 is a cytosine and is labeled;

(P3) an oligonucleotide of 6 to 42 nucleotides comprising a sequence at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% identical to nucleotides 251 to 256 in SEQ ID NO:2, wherein the nucleotide corresponding to the nucleotide at position 256 in SEQ ID NO:2 is a cytosine and is labeled;

(P3') an oligonucleotide of 6 to 42 consecutive nucleotides which hybridizes with the complementary nucleotide sequence to the nucleotides 251 to 256 in SEQ ID NO:2 under stringent conditions, wherein the nucleotide complementary to the nucleotide at position 256 in SEQ ID NO:2 is a cytosine and is labeled.

The (P2) and (P2') probes of the present disclosure may be prepared in the same manner as the quenching probe described in JP 2002-119291 A except that the probes of the present disclosure have the above-described specific sequence in the nucleotide sequence shown in SEQ ID NO:2. Examples of the length of the probes of the present disclosure include 13 to 48 consecutive nucleotides, 13 to 28 consecutive nucleotides, 13 to 23 consecutive nucleotides and 13 to 18 consecutive nucleotides.

Examples of the nucleotide sequences of the (P2) and (P2') probes used in the present disclosure include 5'-gcatgTaaact-tatctcc-3' (SEQ ID NO:4), and the nucleotide denoted by the upper case letter T corresponds to (i.e. is complementary to) the nucleotide at position 251.

The (P3) probe of the present disclosure is a probe for detecting the polymorphism rs1127354 in the ITPA gene, and is composed of an oligonucleotide comprising a nucleotide sequence of 6 to 42 consecutive nucleotides containing nucleotides 251 to 256 in SEQ ID NO:2 or a homologous sequence thereof, wherein the nucleotide corresponding to the nucleotide at position 256 is a cytosine. In some embodiments, the nucleotide corresponding to the nucleotide at position 256 is labeled with a fluorescent dye. As referred to in this context, the homologous sequence is homologous to SEQ ID NO:2 or the recited portion of SEQ ID NO:2. The 6 to 42 nucleotides are all contained, consecutively in SEQ ID NO:2 or its homologous sequence.

The (P3') probe of the present disclosure is a probe for detecting the polymorphism rs1127354 in the ITPA gene, and is composed of an oligonucleotide comprising a nucleotide sequence of 6 to 42 consecutive nucleotides containing nucleotides 251 to 256 in SEQ ID NO:2 or a nucleotide sequence which hybridizes with the complementary strand of SEQ ID NO: 2 under stringent conditions, wherein the nucleotide corresponding to the nucleotide at position 256 is a cytosine. In some embodiments, the nucleotide corresponding to the nucleotide at position 256 is labeled with a fluorescent dye. As referred to in this context, the hybridizing sequence hybridizes with the complementary strand of SEQ ID NO:2 or the recited portion of SEQ ID NO:2. The 6 to 42 nucleotides are all contained, consecutively in SEQ ID NO:2 or the hybridizing sequence.

The polymorphism rs1127354 in the ITPA gene described herein is located at nucleotide position 251 in SEQ ID NO:2. For example, in the (P3) and (P3') probes of the present disclosure, the nucleotide at position 251 in SEQ ID NO:2 is C, which is the wild-type nucleotide.

The (P3) and (P3') probes of the present disclosure may be prepared in the same manner as the quenching probe described in JP 2002-119291 A except that the probes of the present disclosure have the above-described specific sequence in the nucleotide sequence shown in SEQ ID NO:2. Examples of the length of the probes of the present disclosure include 6 to 72 consecutive nucleotides, 6 to 42 consecutive nucleotides, 6 to 27 consecutive nucleotides and 6 to 22 consecutive nucleotides.

Examples of the nucleotide sequences of the (P3) and (P3') probes used in the present disclosure include 5'-tctag-gagataagtttCcatgc-3' (SEQ ID NO 5), and the nucleotide denoted by the upper case letter C corresponds to the nucleotide at position 251.

The fluorescent dye is not restricted, and examples of the fluorescent dye include fluorescein, phosphor, rhodamine and polymethine dye derivatives. Examples of commercially available fluorescent dyes include BODIPY FL (trademark; manufactured by Molecular Probes), FluorePrime (trade name; manufactured by Amersham Pharmacia), Fluoredite (trade name; manufactured by Millipore), FAM (manufactured by ABI), Cy3 and Cy5 (manufactured by Amersham Pharmacia) and TARMA (manufactured by Molecular Probes). The conditions for detection using the probe are not restricted, and may be appropriately determined depending on the fluorescent dye used. The detection may be carried out, for example, with a detection wavelength of 445 to 480 nm in the case of Pacific Blue, with a detection wavelength of 585 to 700 nm in the case of TAMRA, and with a detection wavelength of 520 to 555 nm in the case of BODIPY FL. By using such a probe, hybridization and dissociation may be easily detected based on fluctuation of the signal. The fluorescent dye may be bound to the oligonucleotide by a conventional method such as the one described in JP 2002-119291 A.

The "homologous sequence" in the present application means a nucleotide sequence having an identity of, for example, not less than 80%, 85%, 90%, 95%, 96%, 97%, 98% or 99% to a particular nucleotide sequence (e.g. SEQ ID NO: 1 or 2 or a recited portion thereof) or to the complementary strand (or recited portion thereof) of a specific nucleotide sequence. The identity may also be 100% in the present application.

The hybridization described herein may be carried out according to a known method or a method corresponding thereto, such as the method described in Molecular Cloning 3rd (J. Sambrook et al., Cold Spring Harbor Lab. Press, 2001). This literature is hereby incorporated in the present specification by reference. In some embodiments, said hybridization is under stringent conditions.

The term "stringent conditions" means conditions under which a specific hybrid is formed while nonspecific hybrids are not formed. Typical examples of stringent conditions include conditions under which hybridization is performed with a potassium concentration of about 25 mM to about 50 mM and a magnesium concentration of about 1.0 mM to about 5.0 mM. Examples of the conditions in the present disclosure include conditions under which hybridization is performed in Tris-HCl (pH 8.6), 25 mM KCl and 1.5 mM $MgCl_2$, but the conditions are not limited thereto. Other examples of stringent conditions include those described in Molecular Cloning 3rd (J. Sambrook et al., Cold Spring Harbor Lab. Press, 2001). This literature is hereby incorporated in the present specification by reference. Those skilled in the art may easily select such conditions by, for example, controlling the hybridization reaction and/or changing salt concentrations of the hybridization reaction solution.

Examples of the oligonucleotide of the above fluorescently labeled oligonucleotide include oligonucleotides as well as modified oligonucleotides.

Examples of the constituent units of the above oligonucleotide include ribonucleotides, deoxyribonucleotides and artificial nucleic acids. Examples of the artificial nucleic acids include DNA; RNA; LNA (Locked Nucleic Acid), which is an RNA analogue; PNA (Peptide Nucleic Acid), which is a peptide nucleic acid; and BNA (Bridged Nucleic Acid), which is a bridged nucleic acid.

The oligonucleotide may be constituted by either a single type of constituent unit or a plurality of types of constituent units among the above constituent units.

Each of the (P1) and (P1') probes of the present disclosure has a sequence homologous to a nucleotide sequence of 7 to 28 consecutive nucleotides containing nucleotides 301 to 307 in SEQ ID NO:1, and has homology to SEQ ID NO:1. That is, each of the (P1) and (P1') probes of the present disclosure is homologous, but does not need to be completely identical, to the nucleotide sequence of 7 to 28 consecutive nucleotides containing nucleotides 301 to 307 in SEQ ID NO:1. Further, in some embodiments, the nucleotide corresponding to position 307 is cytosine and/or fluorescently labeled.

Each of the (P2) and (P2') probes of the present disclosure has homology to a complement of a nucleotide sequence of 13 to 28 consecutive nucleotides containing nucleotides 239 to 251 in SEQ ID NO:2. That is, each of the probes (P2) and (P2') of the present disclosure is complementary, but does not need to be completely complementary, to a nucleotide sequence of 13 to 28 consecutive nucleotides containing nucleotides 239 to 251 in SEQ ID NO:2. Further, in some embodiments, the nucleotide corresponding to position 239 is a cytosine and/or is fluorescently labeled.

Each of the (P3) and (P3') probes of the present disclosure has a sequence homologous to a nucleotide sequence of 6 to 42 consecutive nucleotides containing nucleotides 251 to 256 in SEQ ID NO:2, and has homology to SEQ ID NO:2. That is, each of the probes (P3) and (P3') of the present disclosure is homologous, but does not need to be completely identical, to the nucleotide sequence of 6 to 42 consecutive nucleotides containing nucleotides 251 to 256 in SEQ ID NO:2. Further, in some embodiments, the nucleotide corresponding to position 256 is a cytosine and/or is fluorescently labeled.

For example, the fluorescence intensity of the fluorescently labeled oligonucleotide decreases (or the fluorescence is quenched) or increases when the oligonucleotide is hybridized with a complementary sequence, relative to the fluorescence intensity observed when the oligonucleotide is not hybridized with the complementary sequence. For example, the fluorescence intensity of the fluorescently labeled oligonucleotide decreases when the oligonucleotide is hybridized with a complementary sequence, relative to the fluorescence intensity observed when the oligonucleotide is not hybridized with the complementary sequence. A probe that utilizes such fluorescence quenching phenomenon is generally called a guanine quenching probe, and is known as a QProbe (registered trademark). For example, the probe is an oligonucleotide which is designed such that the oligonucleotide has C at its 3'-end or 5'-end and which is fluorescently labeled such that the emission decreases when the terminal C is close to G.

For example, the probe of the present disclosure may be labeled at its 3'-end with a fluorescent dye.

In the present specification, when the term "first, second or third position counted from the 3'-end" is mentioned, the 3'-end is regarded as the first position.

In the detection method described herein, nucleic acid comprising the polymorphism rs8099917 in the IL28B gene and/or the polymorphism rs1127354 in the ITPA gene is analyzed using a nucleic acid probe(s) labeled with a fluorescent dye(s) by measuring fluorescence from the fluorescent dye(s), and melting curve analysis is carried out, followed by detecting the polymorphism(s) based on the result of the melting curve analysis, which nucleic acid probe(s) is/are probe(s) of the present invention.

For example, the detection method of the present invention uses the probe of the present invention and comprises the following steps:

(I) adding the probe of the present invention to a sample containing DNA and allowing hybridization of the probe with the DNA;

(II) changing the temperature to dissociate the hybridization complex between the DNA and the probe, and measuring the fluctuation of the signal due to the dissociation of the hybridization complex;

(III) analyzing the fluctuation of the signal to determine the Tm value; and (IV) determining based on the Tm value the presence/absence of the polymorphism of interest or the abundance ratio of the nucleotide sequence having the polymorphism.

The evaluation of the Tm value in (III) includes not only evaluation of the dissociation temperature of the hybridization complex but also evaluation of the differential value of the fluorescence signal, which fluctuates upon melting of the hybridization complex depending on the temperature. Based on the differential value, the abundance ratio of the nucleotide sequence (DNA) having the polymorphism may be evaluated.

Examples of the method of nucleic acid amplification include methods using a polymerase, such as PCR, ICAN and LAMP. When the amplification is carried out by a method using a polymerase, the amplification may be carried out in the presence of the probe of the present disclosure. Those skilled in the art may easily control reaction conditions and the like of the amplification depending on the probe to be used. By this, the detection may be carried out just by analyzing the Tm value of the probe after the amplification of the nucleic acid, so that the amplification product does not need to be handled after the reaction. Therefore, there is no risk of contamination of the amplification product. Further, since the detection may be carried out with the same apparatus as the one necessary for the amplification, it is not necessary to transfer the container. Therefore, automation may also be easily done.

As the DNA polymerase to be used for the PCR method, a conventional DNA polymerase may be used without any limitation. Examples of the DNA polymerase include GeneTaq (manufactured by Nippon Gene Co., Ltd.), PrimeSTAR Max DNA Polymerase (manufactured by Takara Bio Inc.) and Taq Polymerase.

The amount of the polymerase to be used is not restricted as long as the polymerase is used at a concentration which is normally employed. For example, in cases where Taq polymerase is used, the concentration of the polymerase may be 0.01 U to 100 U per 50 µl of the reaction solution. Use of the polymerase in such an amount has an advantage, for example, in that a sufficient amount of amplified product may be obtained.

In the present disclosure, the DNA in the sample may be either single-stranded DNA or double-stranded DNA. In cases where the DNA is double-stranded DNA, for example, the step of dissociating the double-stranded DNA in the sample by heating may be included before the hybridization step. By dissociating the double-stranded DNA into single-stranded DNA, hybridization with the fluorescently labeled oligonucleotide is possible.

In the present disclosure, the ratio (molar ratio) of the probe of the present disclosure to be added with respect to the DNA in the sample is not restricted, and the ratio is, for example, not more than 1 or not more than 0.3 with respect to the DNA in the sample to ensure a sufficient detection signal. In this case, for example, the DNA in the sample may be either: the sum of the target DNA, wherein the polymorphism to be detected is present, and non-target DNA, wherein the polymorphism to be detected is absent; or the sum of the amplification product containing the target sequence, wherein the polymorphism to be detected is present, and the amplification product containing the non-target sequence, wherein the polymorphism is absent. Although the ratio of the DNA to be detected relative to the DNA in the sample is usually not known, the ratio (molar ratio) of the probe to be added with respect to the DNA to be detected (the amplification product containing the sequence to be detected) is, for example, not more than 100, not more than 50, or not more than 30, as a result. The lower limit of the ratio is not restricted, and the ratio is, for example, not less than 0.001, not less than 0.01, or not less than 0.2. The ratio of the probe of the present disclosure to be added with respect to the DNA may be, for example, either the molar ratio with respect to the double-stranded DNA or the molar ratio with respect to the single-stranded DNA.

The Tm value will now be described. Heating a solution containing double-stranded DNA causes an increase in absorbance at 260 nm. This is caused because the hydrogen bonds between the strands of the double-stranded DNA are broken by the heat and the double-stranded DNA is dissociated into single-stranded DNA (melting of DNA). When the double-stranded DNA is completely dissociated into single-stranded DNA, the absorbance is about 1.5-fold higher than the absorbance at the beginning of heating (absorbance for only the double-stranded DNA), and completion of the melting may be judged by such a change in absorbance. Based on this phenomenon, the melting temperature Tm is generally defined as the temperature at which the increase in absorbance reached 50% of the total increase in absorbance.

In the present disclosure, measurement of the signal fluctuation due to the temperature change for determination of the Tm value may be carried out also by measuring absorbance at 260 nm based on the above-mentioned principle, but the measurement may be carried out based on a signal from a label added to the probe of the present disclosure, which signal fluctuates depending on the state of hybrid formation between the DNA and the probe. Therefore, for example, as the probe of the present disclosure, the above-mentioned labeled probe may be used. Examples of the labeled probe include a fluorescently labeled oligonucleotide probe which emits fluorescence when it is not hybridized with the target sequence, whose fluorescence intensity decreases (or the fluorescence is quenched) when the probe is hybridized with the target sequence, and a fluorescently labeled oligonucleotide probe which emits fluorescence when it is not hybridized with the target sequence, whose fluorescence intensity increases when the probe is hybridized with the target sequence. In the case of the former probe, the probe shows no signal or shows a weak signal when it forms a hybrid (double-stranded DNA) with the sequence to be detected, while the probe shows a signal or the signal increases when the probe is released by heating. In the case of the latter probe, the probe shows a signal when forming a hybrid (double-stranded DNA) with the sequence to be detected, while the signal decreases (disappears) when the probe is released by heating. Therefore, by detecting the change in the signal from the label under conditions specific to the signal (by investigating absorbance or the like), the progress of melting and the Tm value may be determined in a similar manner to the measurement of absorbance at 260 nm. For example, the labeling substance in the labeled probe is as mentioned above, and the probe may be labeled with a fluorescent dye.

The method of the present disclosure for detecting a polymorphism will now be described focusing on the method of detection of changes in the signal from a fluorescent dye. It should be noted that the method of the present disclosure for detecting a polymorphism is characterized by the use per se of the probe for detection of a polymorphism, and other steps and conditions are not restricted.

The range of the temperature at which fluctuation of the fluorescence intensity is measured is not restricted, and the starting temperature may be, for example, room temperature to 85° C., or 25° C. to 70° C., and the end temperature may be, for example, 40° C. to 105° C. The heating rate is not restricted, and may be, for example, 0.1° C./second to 20° C./second, or 0.3° C./second to 5° C./second.

The fluctuation of the signal is then analyzed to determine the Tm value. More particularly, the differential value at each temperature (−d fluorescence intensity/dt) is calculated based on the obtained fluorescence intensity, and the temperature at which the value is lowest may be determined as the Tm value. Further, the point at which the amount of increase in the fluorescence intensity per unit time (the amount of increase in the fluorescence intensity/t) is largest may also be determined as the Tm value. In cases where, as the labeled probe, a probe with which the signal intensity increases upon hybrid formation is used instead of a quenching probe, the amount of decrease in the fluorescence intensity may be measured instead.

In the present disclosure, the hybridization complex is heated and fluorescence signal fluctuation (for example, increase in the fluorescence intensity) due to the increase in the temperature is measured as described above, but, instead of employing this method, signal fluctuation upon formation of the hybrid may be measured, for example. That is, the fluorescence signal fluctuation caused by formation of the hybridization complex due to the decrease in the temperature of the sample to which the probe was added may be measured.

For example, in cases where a fluorescently labeled oligonucleotide probe whose fluorescence intensity is lower (or whose fluorescence is quenched) when the probe is hybridized with the complementary sequence than when the probe is not hybridized with the complementary sequence (e.g., QProbe) is used, the fluorescence intensity is high upon addition of the probe to the sample since the probe is in the dissociated state, while the fluorescence decreases (or is quenched) upon formation of a hybridization complex due to the decrease in the temperature. Therefore, for example, the temperature of the heated sample may be gradually decreased, to measure the decrease in the fluorescence intensity due to the temperature decrease.

On the other hand, in cases where a labeled probe whose signal increases upon formation of the hybrid is used, the fluorescence intensity is low (or the fluorescence is quenched) upon addition of the probe to the sample since the probe is in the dissociated state, while the fluorescence intensity increases upon formation of a hybridization complex due to the decrease in the temperature. Therefore, for example, the temperature of the sample may be gradually decreased, to measure the increase in the fluorescence intensity due to the temperature decrease.

The nucleic acid to be used as a template for carrying out the nucleic acid amplification is not restricted as long as it contains a nucleic acid, and examples of the nucleic acid include those derived from, or those which may be derived from, arbitrary biological origins such as blood; oral mucosal suspensions; somatic cells of nails, hair and the like; germ cells; milk; ascitic fluid; paraffin-embedded tissues; gastric juices; fluids obtained by gastric lavage; peritoneal fluid; amniotic fluid; and cell cultures. The nucleic acid as a template may be used as it is directly after being obtained from any of the above-described origins, or may be pretreated to modify properties of the sample before being used. For example, in cases where whole blood is used as a sample, isolation of the genomic DNA from the whole blood may be carried out by a known method. For example, a commercially available genomic DNA isolation kit (trade name, GFX Genomic Blood DNA Purification kit; manufactured by GE Healthcare Bio-Sciences KK) or the like may be employed.

The primer pair used in the PCR is not restricted as long as a region with which the probe of the present disclosure may be hybridized is amplified. Those skilled in the art may easily design such a primer pair based on the nucleotide sequences of SEQ ID NO:1 or SEQ ID NO:2. The length and the Tm value of each primer are usually 12-mer to 40-mer and 40 to 70° C., or 16-mer to 30-mer and 55 to 60° C., respectively.

The primers in the primer pair do not need to have the same length, but the Tm values of these primers are almost the same (or the difference is not more than 5° C.), for example.

The Tm analysis may be carried out in the same manner as the conventional method except that fluorescence from the fluorescent dye of the probe of the present disclosure is measured. The fluorescence may be measured using the excitation light having a wavelength dependent on the fluorescent dye, and measuring the light having the emission wavelength. The heating rate in the Tm analysis is usually 0.1 to 1° C./second. The composition of the reaction solution used for carrying out the Tm analysis is not restricted as long as the probe may hybridize with a nucleic acid having the complementary sequence of the nucleotide sequence of the probe, and usually, the concentration of monovalent cations is 1.5 to 5 mM, and the pH is 7 to 9. Since the reaction solution in an amplification method using a DNA polymerase, such as PCR, usually satisfies these conditions, the reaction solution after the amplification may be used as it is for the Tm analysis.

Detection of the polymorphism rs8099917 in the IL28B gene and/or the polymorphism rs1127354 in the ITPA gene may be carried out based on the result of the Tm analysis, by a conventional method. The detection in the present disclosure includes detection of the presence/absence of a mutation.

Since detection of the presence/absence of a mutation is possible by the method of the present disclosure using the probe of the present disclosure, the present invention also includes judgment (or prediction) of the pharmacological effect of a therapeutic agent against hepatitis C virus and judgment (or prediction) of tolerance to a therapeutic agent against hepatitis C virus. More specifically, in cases where the nucleotides at the polymorphism rs8099917 in the IL28B gene are T (T/T), which corresponds to the wild-type, the pegylated interferon+ribavirin combination therapy is suggested to be effective, while in cases where rs8099917 has G, which corresponds to the mutant type (G/G or T/G), the therapy is suggested to be ineffective. In cases where the nucleotides at the polymorphism rs1127354 in the ITPA gene comprise A, which corresponds to the mutant type (A/A or C/A), it is suggested that severe anemia as a side effect of ribavirin is unlikely to occur and therefore administration of ribavirin at a high dose is possible.

Further, by the method of the present disclosure, simultaneous detection of the polymorphism rs8099917 in the IL28B gene and the polymorphism rs1127354 in the ITPA gene is also possible.

<2> Kit

The kit of the present disclosure is a kit to be used for the detection method of the present disclosure. This kit may comprise a nucleic acid probe composed of the above-described oligonucleotide. In some embodiments, the probe is labeled with a fluorescent dye whose fluorescence changes upon hybridization (e.g., quenching probe). The kit of the present disclosure may also be used for judging (or predicting) the pharmacological effect of a therapeutic agent against hepatitis C virus and tolerance to a therapeutic agent against hepatitis C virus.

The detection kit of the present disclosure may further comprise, in addition to the probe, reagents required for nucleic acid amplification in the detection method of the present disclosure, especially primers for amplification using a DNA polymerase.

More specifically, the primers of the present disclosure are primers for amplifying a region in the nucleotide sequence shown in SEQ ID NO:1 in the IL28B gene, which region comprises a sequence with which the P1 or P1' oligonucleotide hybridizes, and/or primers for amplifying a region in the nucleotide sequence shown in SEQ ID NO:2 in the ITPA gene, which region comprises a sequence with which the P2, P2', P3, or P3' oligonucleotide hybridizes.

The detection kit of the present disclosure may comprise the probe, primers and other reagents separately or as a mixture(s) of a part of these components.

The present invention is described more concretely by way of Examples below. However, these Examples are merely examples and the present invention is not limited to the Examples.

In the present disclosure, in terms of the individual sequences of the sample nucleic acid in the sample to be subjected to the detection, and the probes and primers for detecting polymorphisms, matters described herein based on the complementary relationship between these sequences are applied to the respective sequences and also to the sequences complementary thereto unless otherwise specified. When the matters of the present disclosure are applied to the sequence complementary to each sequence, the sequence recognized by the complementary sequence is read as the sequence complementary to the corresponding sequence described in the present specification throughout the specification according to the common technical knowledge.

EXAMPLES

Example 1

Use of a Single Probe for Detection of Template Oligonucleotide for IL28B

Based on the nucleotide sequence (SEQ ID NO:1) comprising the polymorphic site rs8099917 in the IL28B gene, the probe shown in Table 1 having C at its 3'-end was designed. In Table 1, the position of the probe is represented by nucleotide positions in the nucleotide sequence shown in SEQ ID NO:1. Labeling with BODIPY FL was carried out according to a conventional method.

The sequences of the template oligonucleotides used as the subject sequences to be detected (mutant type (SEQ ID NO:10) and wild-type (SEQ ID NO:11)) are shown in Table 1. In Table 1, the position of each oligonucleotide is represented by nucleotide positions in the nucleotide sequence shown in SEQ ID NO:1. A mixture of the template oligonucleotides of SEQ ID NOs:10 and 11 at a ratio of 1:1 was used as a sample for studying the heterozygous sample.

Using the reagents described below and a fully automatic SNPs testing device (trade name: i-densy (registered trademark), manufactured by ARKRAY, Inc.), Tm analysis was carried out to evaluate the performance of the fluorescently labeled oligonucleotide (SEQ ID NO:3).

In the Tm analysis, treatment was carried out at 95° C. for 1 second and then at 40° C. for 60 seconds, followed by increasing the temperature from 40° C. to 85° C. with a heating rate of 1° C./3 seconds, while measuring changes in the fluorescence intensity with time. The excitation wavelength and detection wavelength in the Tm analysis were 420 to 485 nm and 520 to 555 nm, respectively (BODIPY FL).

TABLE 2

| (Reaction solution volume: 50 μl) | |
| --- | --- |
| 1 × Gene Taq Universal buffer (manufactured by Nippon Gene Co., Ltd.) | |
| IL28B(917) probe | 0.2 μM |
| Template oligonucleotide | 0.2 μM |

Figure 2:
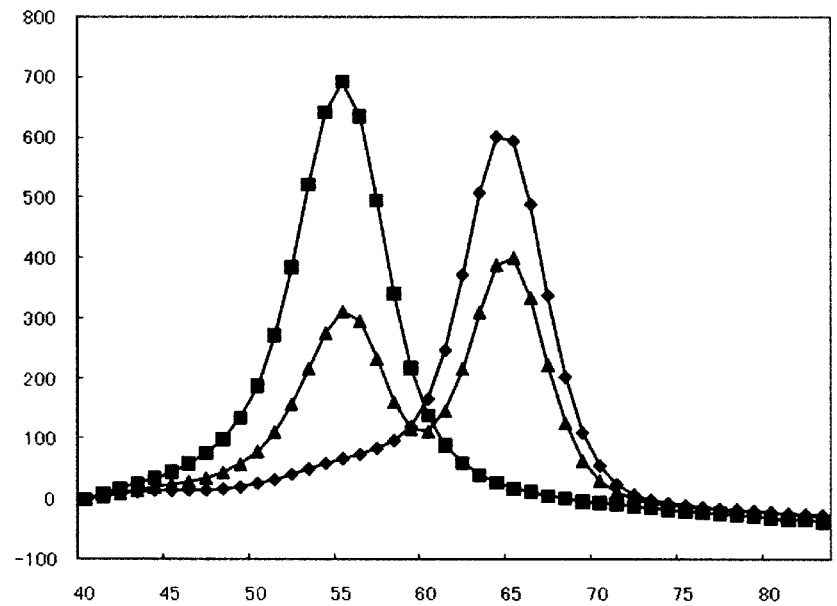
FIG. 2 shows melting curves obtained using the probes of Example 1 of the present disclosure for detecting a polymorphism. The amount of change in the fluorescence intensity per unit time is plotted along the ordinate (d the amount of increase in the fluorescence intensity/t) and the temperature (° C.) is plotted along the abscissa. Squares represent the wild-type, diamonds represent the mutant type, and triangles represent the heterozygous type (this also applies to the figures below).

As a result of the Tm analysis using the probe shown in Table 1, the peak for BODIPY FL was found at about 55° C. in the case of the wild-type oligonucleotide (squares), and at about 64° C. in the case of the mutant type oligonucleotide (diamonds) (FIG. 2). The heterozygous oligonucleotide (triangles) wherein the wild-type and the mutant type are mixed showed peaks for BODIPY FL at about 55° C. and about 64° C. (FIG. 2).

As described above, it was revealed that the wild-type (T/T), heterozygous type (T/G) and mutant type (G/G) may be distinguished from one another since these clearly show unique patterns of peaks.

Comparative Example 1

Use of a Single Probe for Detection of Template Oligonucleotide for IL28B

Based on the nucleotide sequence (SEQ ID NO:1) comprising the polymorphic site rs8099917 in the IL28B gene, the probe shown in Table 3 having C at its 3'-end was designed. In Table 3, the position of the probe is represented by nucleotide positions in the nucleotide sequence shown in SEQ ID NO:1. Labeling with BODIPY FL was carried out according to a conventional method.

The sequences of the template oligonucleotides used as the subject sequences to be detected (mutant type (SEQ ID NO:13) and wild-type (SEQ ID NO:14)) are shown in Table 3. In Table 3, the position of each oligonucleotide is represented by nucleotide positions in the nucleotide sequence shown in SEQ ID NO:1. A mixture of the template oligonucleotides of SEQ ID NOs:13 and 14 at a ratio of 1:1 was used as a sample for studying the heterozygous sample.

TABLE 1

| Name | Sequence (5'→3') | Position | SEQ ID NO: | mer | GC content (%) | Tm (mt) | Tm (WT) | ΔTm |
| --- | --- | --- | --- | --- | --- | --- | --- | --- |
| IL28B(917) probe | ctgtgagcaatGtcaccc-(BODIPY FL) | 290-307 | 3 | 18 | 55.6 | 52.1 | 44.3 | 7.8 |

*The nucleotide denoted by the upper case letter indicates the position of the mutation.

| Template oligonucleotide | Sequence (5'→3') | Position | SEQ ID NO: | mer |
| --- | --- | --- | --- | --- |
| Mutant type | tggttccaatttgggtgaCattgctcacagaaaggaa | 319-283 | 10 | 37 |
| Wild-type | tggttccaatttgggtgaAattgctcacagaaaggaa | 319-283 | 11 | 37 |

*The nucleotides denoted by the upper case letters indicate the position of the mutation.

TABLE 3

| Name | Sequence (5'→3') | Position | SEQ ID NO: | mer | GC content (%) | Tm (mt) | Tm (WT) | ΔTm |
|---|---|---|---|---|---|---|---|---|
| IL28B(0917) probe2 | caatttgggtgaCattgctc-(BODIPY FL) | 313-294 (Complementary strand) | 12 | 20 | 45 | 51.7 | 43.2 | 8.5 |

*The nucleotide denoted by the upper case letter indicates the position of the mutation.

| Template oligonucleotide | Sequence (5'→3') | Position | SEQ ID NO: | mer |
|---|---|---|---|---|
| Mutant type | ttcctttctgtgagcaatGtcacc caaattggaacca | 283-319 | 13 | 37 |
| Wild-type | ttcctttctgtgagcaatTtcacc caaattggaacca | 283-319 | 14 | 37 |

*The nucleotides denoted by the upper case letters indicate the position of the mutation.

Using the reagents described below and a fully automatic SNPs testing device (trade name: i-densy (registered trademark), manufactured by ARKRAY, Inc.), Tm analysis was carried out to evaluate the performance of the fluorescently labeled oligonucleotide (SEQ ID NO:12).

In the Tm analysis, treatment was carried out at 95° C. for 1 second and then at 40° C. for 60 seconds, followed by increasing the temperature from 40° C. to 85° C. with a heating rate of 1° C./3 seconds, while measuring changes in the fluorescence intensity with time. The excitation wavelength and detection wavelength in the Tm analysis were 420 to 485 nm and 520 to 555 nm, respectively (BODIPY FL).

TABLE 4

| (Reaction solution volume: 50 μl) | |
|---|---|
| 1 × Gene Taq Universal buffer (manufactured by Nippon Gene Co., Ltd.) | |
| IL28B(917) probe 2 | 0.2 μM |
| Template oligonucleotide | 0.2 μM |

Figure 3:
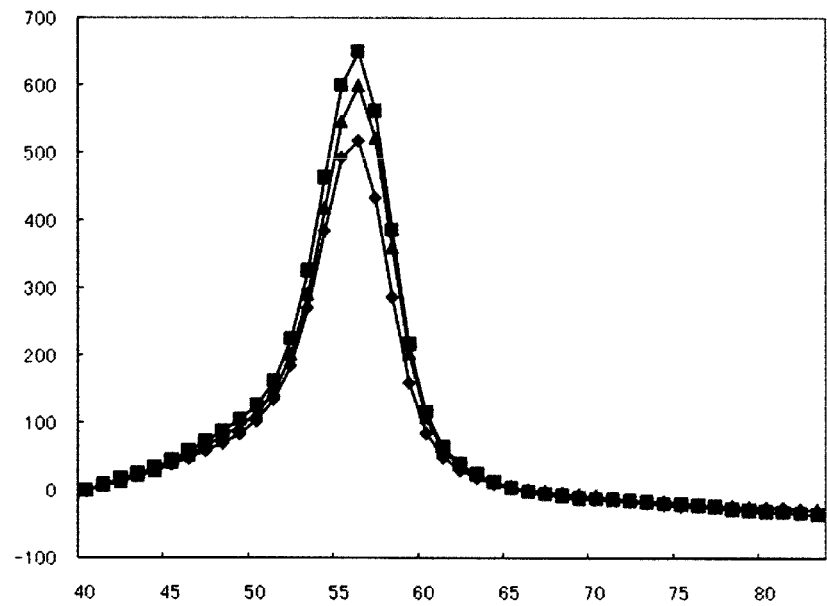
FIG. 3 shows melting curves obtained using the probes of Comparative Example 1 for detecting a polymorphism.

As a result of the Tm analysis using the probe shown in Table 3, the peak for BODIPY FL was found at about 56° C. in the case of the wild-type oligonucleotide (squares), and at about 55° C. in the case of the mutant type oligonucleotide (diamonds) (FIG. 3). Thus, it was revealed that Δ of the Tm value (i.e. the difference between the Tm values) is too small to distinguish between the types.

The heterozygous oligonucleotide (triangles) wherein the wild-type and the mutant type are mixed showed a peak for BODIPY FL only at about 56° C. (FIG. 3). Therefore, it was revealed that the heterozygous type produces only a single detection peak and hence the wild-type and the mutant type cannot be distinguished from each other.

Accordingly, taking the above result into account together with the result of Example 1, it may be understood that fluorescent labeling of C at the 3'-end of the probe sequence is not necessarily effective, and that fluorescent labeling of C at position 307 in the nucleotide sequence shown in SEQ ID NO:1, as is the case of the probe shown in SEQ ID NO:3, is important.

Example 2

Use of a Single Probe for Detection of Template Oligonucleotide for ITPA

Based on the nucleotide sequence (SEQ ID NO:2) comprising the polymorphic site rs1127354 in the ITPA gene, the probe shown in Table 5 having C at its 3'-end was designed. In Table 5, the position of the probe is represented by nucleotide positions in the nucleotide sequence shown in SEQ ID NO:2. Labeling with TAMRA was carried out according to a conventional method.

The sequences of the template oligonucleotides used as the subject sequences to be detected (mutant type (SEQ ID NO:15) and wild-type (SEQ ID NO:16)) are shown in Table 5. In Table 5, the position of each oligonucleotide is represented by nucleotide positions in the nucleotide sequence shown in SEQ ID NO:2. A mixture of the template oligonucleotides of SEQ ID NOs:15 and 16 at a ratio of 1:1 was used as a sample for studying the heterozygous sample.

TABLE 5

| Name | Sequence (5'→3') | Position | SEQ ID NO: | mer | GC content (%) | Tm (mt) | Tm (WT) | ΔTm |
|---|---|---|---|---|---|---|---|---|
| ITPA(354) probe2 | tctaggagataagtttCcatgc-(TAMRA) | 235-256 | 5 | 22 | 40.9 | 41.3 | 50.9 | 9.6 |

*The nucleotide denoted by the upper case letter indicates the position of the mutation.

| Template oligonucleotide | Sequence (5'→3') | Position | SEQ ID NO: | mer |
|---|---|---|---|---|
| Mutant type | ggtcaattttctgtgccaccaaagtgcatgTaaact tatctcctagaatctgaacgacct | 281-222 | 15 | 60 |

TABLE 5-continued

| | | | | |
|---|---|---|---|---|
| Wild-type | ggtcaattttctgtgccaccaaagtgcatgGaaact tatctcctagaatctgaacgacct | 281-222 | 16 | 60 |

*The nucleotides denoted by the upper case letters indicate the position of the mutation.

Using the reagents described below and a fully automatic SNPs testing device (trade name: i-densy (registered trademark), manufactured by ARKRAY, Inc.), Tm analysis was carried out to evaluate the performance of the fluorescently labeled oligonucleotide (SEQ ID NO:5).

In the Tm analysis, treatment was carried out at 95° C. for 1 second and then at 40° C. for 60 seconds, followed by increasing the temperature from 40° C. to 85° C. with a heating rate of 1° C./3 seconds, while measuring changes in the fluorescence intensity with time. The excitation wavelength and detection wavelength in the Tm analysis were 520 to 555 nm and 585 to 700 nm, respectively (TAMRA).

positions in the nucleotide sequence shown in SEQ ID NO:2. Labeling with TAMRA was carried out according to a conventional method.

The sequences of the template oligonucleotides used as the subject sequences to be detected (wild-type (SEQ ID NO:18) and mutant type (SEQ ID NO:19)) are shown in Table 7. In Table 7, the position of each oligonucleotide is represented by nucleotide positions in the nucleotide sequence shown in SEQ ID NO:2. A mixture of the template oligonucleotides of SEQ ID NOs:18 and 19 at a ratio of 1:1 was used as a sample for studying the heterozygous sample.

TABLE 7

| Name | Sequence (5'→3') | Position | SEQ ID NO: | mer | GC content (%) | Tm (mt) | Tm (WT) | ΔTm |
|---|---|---|---|---|---|---|---|---|
| 3T-ITPA-94A-F1-TK | cagattctaggagataagtttCc-(TAMRA) | 230-252 | 17 | 23 | 39.1 | 40.4 | 49.6 | 9.2 |

*The nucleotide denoted by the upper case letter indicates the position of the mutation.

| Template oligonucleotide | Sequence (5'→3') | Position | SEQ ID NO: | mer |
|---|---|---|---|---|
| Wild-type (ITPA-RG) | tgGaaacttatctcctagaatctga | 253-229 | 18 | 25 |
| Mutant type (ITPA-RT) | tgTaaacttatctcctagaatctga | 253-229 | 19 | 25 |

*The nucleotides denoted by the upper case letters indicate the position of the mutation.

TABLE 6

(Reaction solution volume: 50 μl)

| | |
|---|---|
| 1 × Gene Taq Universal buffer (manufactured by Nippon Gene Co., Ltd.) | |
| ITPA(354) probe 2 | 0.2 μM |
| Template oligonucleotide | 0.2 μM |

Figure 4:
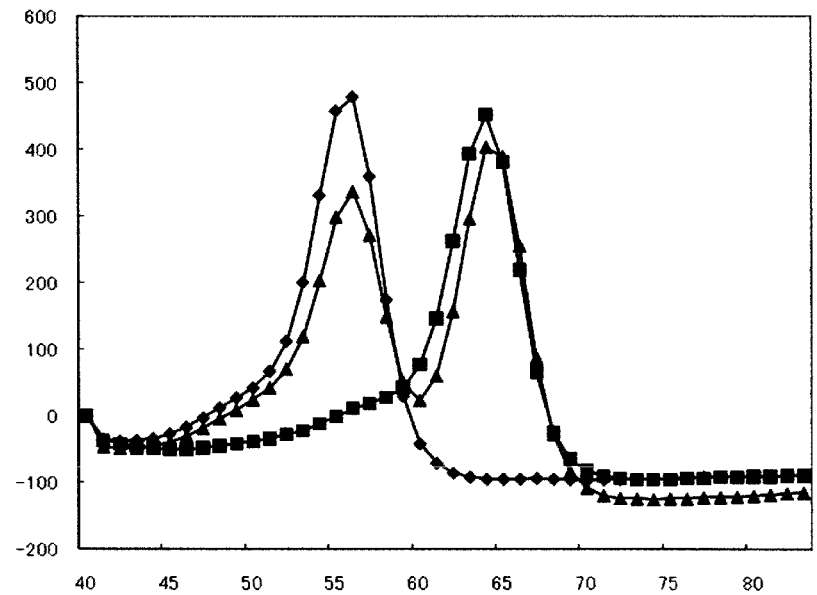
FIG. 4 shows melting curves obtained using the probes of Example 2 of the present disclosure for detecting a polymorphism.

As a result of the Tm analysis using the probe shown in Table 5, the peak for TAMRA was found at about 64° C. in the case of the wild-type oligonucleotide (squares), and at about 56° C. in the case of the mutant type oligonucleotide (diamonds) (FIG. 4). Thus, it was revealed that the wild-type and the mutant type may be distinguished from each other.

The heterozygous oligonucleotide (triangles) wherein the wild-type and the mutant type are mixed showed peaks for TAMRA at about 56° C. and about 64° C. (FIG. 4). Therefore, it was revealed that the heterozygous type may be distinguished from the wild-type and the mutant type.

Comparative Example 2

Use of a Single Probe for Detection of Template Oligonucleotide for ITPA

Based on the nucleotide sequence (SEQ ID NO:2) comprising the polymorphic site rs1127354 in the ITPA gene, the probe shown in Table 7 having C at its 3'-end was designed. In Table 7, the position of the probe is represented by nucleotide Using the reagents described below and a fully automatic SNPs testing device (trade name: i-densy (registered trademark), manufactured by ARKRAY, Inc.), Tm analysis was carried out to evaluate the performance of the fluorescently labeled oligonucleotide (SEQ ID NO:17).

In the Tm analysis, treatment was carried out at 95° C. for 1 second and then at 40° C. for 60 seconds, followed by increasing the temperature from 40° C. to 75° C. with a heating rate of 1° C./3 seconds, while measuring changes in the fluorescence intensity with time. The excitation wavelength and detection wavelength in the Tm analysis were 520 to 555 nm and 585 to 700 nm, respectively (TAMRA).

TABLE 8

(Reaction solution volume: 50 μl)

| | |
|---|---|
| 1 × Gene Taq Universal buffer (manufactured by Nippon Gene Co., Ltd.) | |
| 3T-ITPA-94A-F1-TK | 0.2 μM |
| Template oligonucleotide | 0.2 μM |

Figure 5:
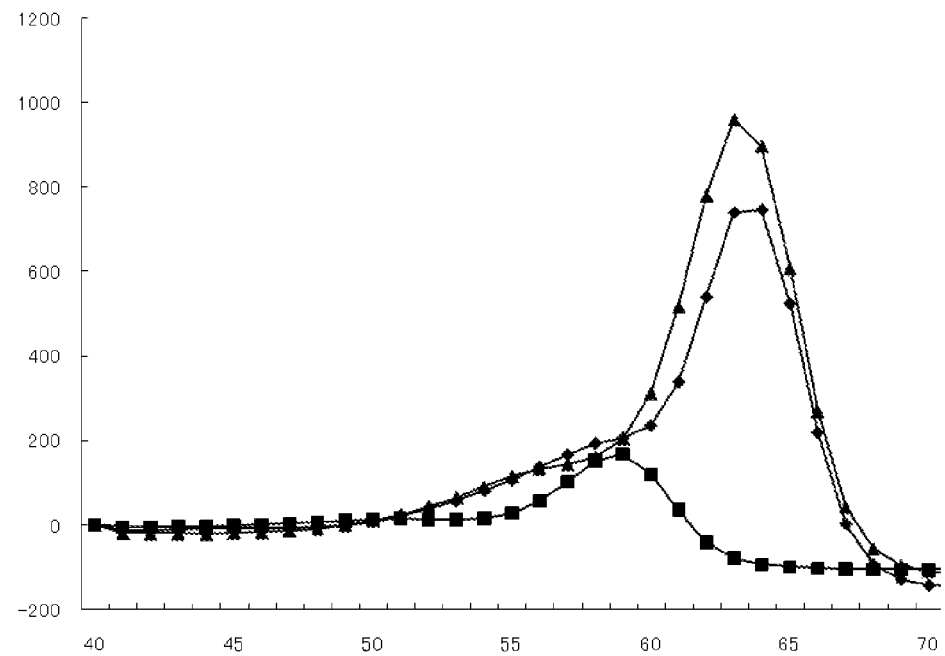
FIG. 5 shows melting curves obtained using the probes of Comparative Example 2 for detecting a polymorphism.

As a result of the Tm analysis using the probe shown in Table 7, the peak for TAMRA was found at about 63° C. in the case of the wild-type oligonucleotide (triangles), and at about 59° C. in the case of the mutant type oligonucleotide (squares) (FIG. 5).

The heterozygous oligonucleotide (diamonds) wherein the wild-type and the mutant type are mixed showed a peak for TAMRA only at about 64° C. (FIG. 5). Therefore, it was revealed that the heterozygous type produces only a single detection peak and hence cannot be distinguished from either the wild-type or the mutant type.

Accordingly, taking the above result into account together with the result of Example 2, it may be understood that fluorescent labeling of C at the 3'-end of the probe sequence is not necessarily effective, and that fluorescent labeling of C at position 256 in the nucleotide sequence shown in SEQ ID NO:2, as is the case of the probe shown in SEQ ID NO:5, is important.

Example 3

Use of a Plurality of Probes for Detection from Purified Human Genomic DNA or Whole Blood Polymorphic regions were amplified as described below from purified human genomic DNA or whole blood by PCR using the primers described below, and Tm analysis was carried out using the probes shown in SEQ ID NOs:3 and 4.

First, the primers shown in Table 9 were designed based on the nucleotide sequence having the polymorphic site rs8099917 in the IL28B gene (SEQ ID NO:1), such that the polymorphic site may be amplified with the primers. In Table 9, the positions of the primers are represented by nucleotide positions in the nucleotide sequence shown in SEQ ID NO:1.

Further, the primers shown in Table 10 were designed based on the nucleotide sequence having the polymorphic site rs1127354 in the ITPA gene (SEQ ID NO:2), such that the polymorphic site may be amplified with the primers. In Table 10, the positions of the primers are represented by nucleotide positions in the nucleotide sequence shown in SEQ ID NO:2.

PCR and Tm analysis were then carried out using a fully automatic SNPs testing device (trade name: i-densy IS-5310, manufactured by ARKRAY, Inc.). The composition of the PCR reaction solution was as described below. As a sample, whole blood or purified human genomic DNA as described below was used. The PCR and Tm analysis were carried out under the following conditions: 95° C. for 60 seconds→(95° C. for 1 second→58° C. for 30 seconds)×50 cycles→95° C. for 1 second→40° C. for 60 seconds→(40° C.→85° C., 1° C./3 seconds).

The excitation wavelength and detection wavelength in the Tm analysis were 420 to 485 nm and 520 to 555 nm, respectively (BODIPY FL), or 520 to 555 nm and 585 to 700 nm, respectively (TAMRA).

TABLE 9

| Name | Sequence (5'→3') | Position | SEQ ID NO: | mer |
|---|---|---|---|---|
| IL28B(917)F | caacatggagagttaaagtaagtcttgtatttcacc | 197-232 | 6 | 36 |
| IL28B(917)R | cagctaccaaactgtatacagcatggttc | 342-314 | 7 | 29 |

| Name | Sequence (5'→3') | Position | SEQ ID NO: | mer | GC content (%) | Tm (mt) | Tm (WT) | ΔTm |
|---|---|---|---|---|---|---|---|---|
| IL28B(917) probe | ctgtgagcaatGtcaccc-(BODIPY FL) | 290-307 | 3 | 18 | 55.6 | 52.1 | 44.3 | 7.8 |

*The nucleotide denoted by the upper case letter indicates the position of the mutation.

TABLE 10

| Name | Sequence (5'→3') | Position | SEQ ID NO: | mer |
|---|---|---|---|---|
| ITPA(354)F | aagtgttctcttttctcttggaacag | 198-223 | 8 | 26 |
| ITPA(354)R | agagacatacggtcaattttctgtg | 291-267 | 9 | 25 |

| Name | Sequence (5'→3') | Position | SEQ ID NO: | mer | GC content (%) | Tm (mt) | Tm (WT) | ΔTm |
|---|---|---|---|---|---|---|---|---|
| ITPA(354) probe | gcatgTaaacttatctcc-(TAMRA) | 256-239 (Complementary strand) | 4 | 18 | 38.9 | 43.9 | 34.1 | 9.8 |

*The nucleotide denoted by the upper case letter indicates the position of the mutation.

TABLE 11

<<For use of purified human genomic DNA as template>>
(Reaction solution volume: 50 μl)

| 1 × PCR buffer | | |
| --- | --- | --- |
| dNTP | 0.2 | mM |
| MgCl$_2$ | 1.5 | mM |
| Taq polymerase (manufactured by ARKRAY, Inc.) | 1.88 | U/test |
| ITPA(354)F | 1 | μM |
| ITPA(354)R | 0.5 | μM |
| IL28B(917)F | 0.5 | μM |
| IL28B(917)R | 1 | μM |
| IL28B(917) probe | 0.2 | μM |
| ITPA(354) probe | 0.2 | μM |
| Purified human genomic DNA* | 100 copies | |

*Human genomic DNA purified from whole blood was used

TABLE 12

<<For use of whole blood as template>>
(Reaction solution volume: 50 μl)

| 1 × PCR buffer | | |
| --- | --- | --- |
| dNTP | 0.2 | mM |
| MgCl$_2$ | 1.5 | mM |
| Taq polymerase (manufactured by ARKRAY, Inc.) | 1.88 | U/test |
| ITPA(354)F | 1 | μM |
| ITPA(354)R | 0.5 | μM |
| IL28B(917)F | 0.5 | μM |
| IL28B(917)R | 1 | μM |
| IL28B(917) probe | 0.2 | μM |
| ITPA(354) probe | 0.2 | μM |
| Pretreated whole blood | (4 μl*) | |

*Pretreated whole blood was used.

<Purified DNA>

Purified DNA was added as a template to the PCR reaction solution such that 100 copies/test of the DNA was contained therein.

<Preparation of Whole Blood>

To 70 μl of dilution buffer (1), 10 μl of whole blood was added, and the resulting mixture was mixed well, followed by adding 10 μl of the resulting mixture to 70 μl of dilution buffer (2). By heating 17 μl of the resulting mixture at 95° C. for 10 minutes, 4 μl of pretreated whole blood was obtained. The pretreated whole blood was added to the PCR reaction solution, to use DNA originating from the pretreated whole blood as a template.

TABLE 13

| Dilution buffer (1) | |
| --- | --- |
| Tris-HCl (pH 8.0) | 10 mM |
| EDTA (pH 8.0) | 0.1 mM |
| SDS | 0.30% |
| Dilution buffer (2) | |
| Tris-HCl (pH 8.0) | 10 mM |
| 500 mM EDTA (pH 8.0) | 0.1 mM |

Figure 6:
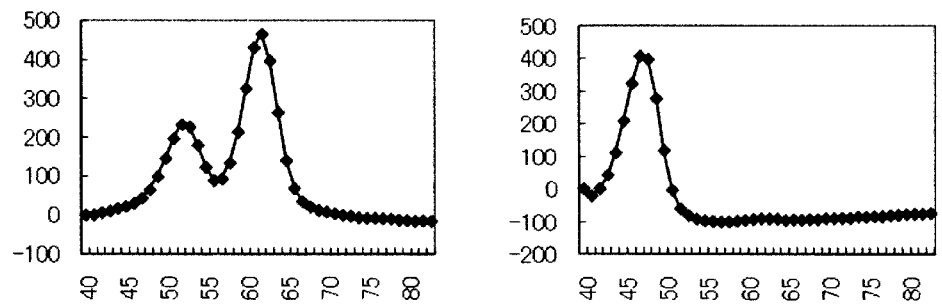
FIG. 6 shows melting curves obtained using the probes of Example 3 of the present disclosure for detecting polymorphisms, together with purified human genomic DNA. The left panel shows a melting curve obtained by detection of a polymorphism in the IL28B gene, and the right panel shows a melting curve obtained by detection of a polymorphism in the ITPA gene (this also applies to the next figure).
Figure 7:
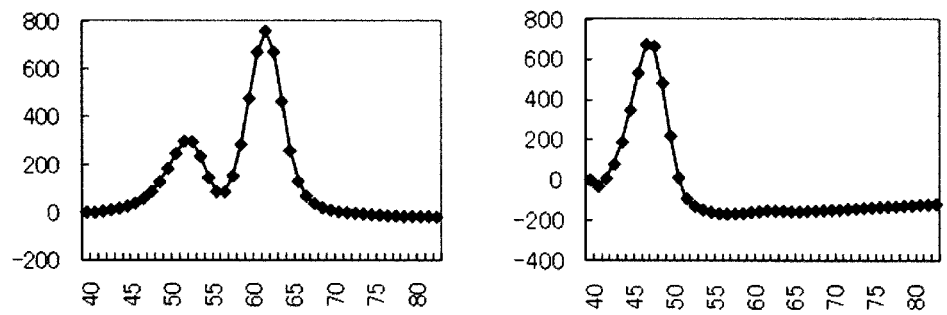
FIG. 7 shows melting curves obtained using the probes of Example 3 of the present disclosure for detecting polymorphisms, together with whole blood.

As a result of the evaluation of the IL28B gene with the fluorescence of BODIPY FL, the peaks for both the wild-type and the mutant type were found for the purified human genomic DNA (FIG. 6, left panel) and the blood (FIG. 7, left panel). Thus, the samples were revealed to have the heterozygous genotype (T/G).

Further, as a result of the evaluation of the ITPA gene with the fluorescence of TAMRA, only the peak for the wild-type was found for the purified human genomic DNA (FIG. 6, right panel) and the blood (FIG. 7, right panel). Thus, the samples were revealed to have the wild-type genotype (C/C).

As may be seen from the results shown in FIGS. 6 and 7, when the probes shown in SEQ ID NOs:3 and 4 were used, changes in the fluorescence intensity that may be analyzed by Tm analysis were observed for the IL28B gene polymorphism and the ITPA gene polymorphism.

That is, in terms of the IL28B gene polymorphism, the purified human genomic DNA and the whole blood having the heterozygous genotype T/G showed two peaks (53° C. and 62° C.) and hence exhibited a unique pattern in respect of the amount of change in the fluorescence intensity.

Further, also in terms of the ITPA gene polymorphism, the purified human genomic DNA and the whole blood showed a single peak (48° C.) and hence exhibited a unique pattern in respect of the amount of change in the fluorescence intensity.

Thus, by using the probes of SEQ ID NOs:3 and 4 simultaneously, the IL28B gene polymorphism and the ITPA gene polymorphism may be detected simultaneously.

Further, since the probe of SEQ ID NO:5 is labeled at C at its 3'-end as in the case of the probe of SEQ ID NO:4 and the effect of the label has been demonstrated in Example 2, it is possible to simultaneously detect the IL28B gene polymorphism and the ITPA gene polymorphism also by simultaneous use of the probe of SEQ ID NO:5 and the probe of SEQ ID NO:3.

INDUSTRIAL APPLICABILITY

The present invention may be suitably used in fields such as healthcare, diagnosis and research.

The invention claimed is:

1. A probe consisting of the nucleotide sequence of SEQ ID NO: 3 and a fluorescent dye attached to the 3' terminal cytosine nucleotide.

2. A probe composition comprising the probe of claim 1 and at least one labeled oligonucleotide selected from P2 and P3 below:
 (P2) an isolated oligonucleotide of 13 to 28 nucleotides comprising a sequence at least 85% identical to the complement of nucleotides 239 to 251 in SEQ ID NO:2, wherein the nucleotide complementary to the nucleotide at position 239 in SEQ ID NO:2 is a cytosine and is labeled;
 (P3) an isolated oligonucleotide of 6 to 42 nucleotides comprising a sequence at least 85% identical to nucleotides 251 to 256 in SEQ ID NO:2, wherein the nucleotide at position 256 in SEQ ID NO:2 is a cytosine and is labeled.

3. The probe according to claim 1, wherein said probe emits fluorescence when said probe is not hybridized with a target sequence, and the fluorescence intensity decreases when said probe is hybridized with said target sequence.

4. A method of detecting the presence of an rs809997 polymorphism in an IL28B gene in a sample comprising nucleic acid, comprising:
 contacting the probe according to claim 1 with said sample, and detecting a hybridization complex between said probe and target nucleic acid in said sample as indicative of the presence of the rs809997 polymorphism.

5. A reagent kit for detecting polymorphisms in the IL28B gene, comprising the probe according to claim 1, wherein said reagent kit further comprises:
 a primer comprising the nucleotide sequence of SEQ ID NO: 6 or 7.

6. The probe composition according to claim 2, wherein the isolated oligonucleotide P2 comprises the complement to nucleotides 239 to 251 in SEQ ID NO:2; and
 the isolated oligonucleotide P3 comprises the sequence of the nucleotides 251 to 256 in SEQ ID NO:2.

7. The probe composition according to claim 2, wherein each of the isolated oligonucleotides P2 and P3 is labeled with a fluorescent dye at the first, second or third position counted from the 3' end of the oligonucleotide.

8. The probe according to claim 1, wherein the fluorescent dye is selected from the group consisting of fluorescein, phosphor, rhodamine, and polymethine dye.

9. The probe composition according to claim 2, wherein
 the isolated oligonucleotide P2 consists of the base sequence of SEQ ID NO: 4 and a label; and
 the isolated oligonucleotide P3 consists of the base sequence of SEQ ID NO: 5 and a label.

10. A method of detecting the presence of an rs809997 polymorphism in an IL28B gene and an rs1127354 polymorphism in an ITPA gene in a sample comprising nucleic acid, comprising:
 contacting the probe composition according to claim 9 with said sample, and detecting hybridization complexes formed between the probes in said probe composition and target nucleic acid in said sample as indicative of the presence of the polymorphisms.

* * * * *